United States Patent [19]

Bhattacharya et al.

[11] Patent Number: 5,332,834
[45] Date of Patent: Jul. 26, 1994

[54] RACEMIZATION OF AN ENANTOMERICALLY ENRICHED α-ARYL CARBOXYLIC ACID

[75] Inventors: Apurba Bhattacharya; John R. Fritch; Carl D. Murphy; Larry D. Zeagler; Carina Araullo-McAdams, all of Corpus Christi, Tex.

[73] Assignee: Hoechst Celanese Corporation, Somerville, N.J.

[21] Appl. No.: 985,083

[22] Filed: Dec. 2, 1992

[51] Int. Cl.⁵ .................. C07D 233/64; C07B 55/00; C07B 57/00; C07C 51/487
[52] U.S. Cl. ......................... 548/339.1; 562/401; 562/490; 562/492; 562/496
[58] Field of Search ................ 562/401, 490, 492; 548/344, 339.1

[56] References Cited

U.S. PATENT DOCUMENTS

| | | | |
|---|---|---|---|
| 3,431,295 | 3/1969 | Suverkropp | 562/401 |
| 4,752,417 | 6/1988 | Inoue et al. | 562/401 |
| 4,946,997 | 8/1990 | Larsen et al. | 562/401 |
| 4,994,604 | 2/1991 | Tung et al. | 562/401 |
| 5,015,764 | 5/1991 | Manimaran et al. | 562/401 |
| 5,221,765 | 6/1993 | Patil et al. | 562/401 |

FOREIGN PATENT DOCUMENTS 0899023 6/1962 United Kingdom.

*Primary Examiner*—José G. Dees
*Assistant Examiner*—Vera C. Clarke
*Attorney, Agent, or Firm*—James J. Mullen; Palaiyur S. Kalyanaraman

[57] ABSTRACT

There is disclosed and claimed a process whereby S(+)-ibuprofen L-lysinate salt is produced by selective precipitation from a mixture containing enantiomers of ibuprofen and L-lysine. The quantity of L-lysine is not more than about a molar equivalent of the quantity of S(+)-ibuprofen in the ibuprofen enantiomeric mixture. The mother liquors after separating the above salt are enriched in R-ibuprofen which is racemized by a novel thermal racemization process and may then be recycled.

3 Claims, 4 Drawing Sheets

LYSINE REMOVAL BY
SECOND CROP CRYSTALLIZATION

LYSINE REMOVAL BY
AQUEOUS EXTRACTION

LYSINE REMOVAL BY EXTRACTION WITH AQUEOUS ACID

FREE S(+)-IBUPROFEN FROM LYSINATE SALT

REMOVAL OF HOAc FROM LYSINE ACETATE

REMOVAL OF HOAc FROM LYSINE ACETATE WITH IBUPROFEN

RACEMIZATION OF AN ENANTOMERICALLY ENRICHED α-ARYL CARBOXYLIC ACID

FIELD OF THE INVENTION

The present invention relates to selective crystallization of the desired salt of an α-aryl carboxylic acid from a mixture containing an α-aryl carboxylic acid and a suitable amino acid. By appropriate choice of the amounts of reactants, the process enables selective crystallization of the desired diastereomer salt. Repetition of this process affords high yields of the desired salt in good enantiomeric excess, which may then be optionally acidified to afford optically active α-aryl carboxylic acid.

BACKGROUND OF THE INVENTION

α-Aryl carboxylic acids are well known non-steroidal anti-inflammatory (NSAI) drugs. An example is ibuprofen (Formula 1) which is typically a racemic mixture of the S(+)- and R(−)-enantiomers.

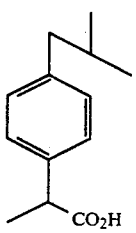

1

Studies have indicated that the S(+)-isomer is more pharmacologically active than the R(−)-isomer, see, for Example. A. Avgerinos et al, *Chirality*, Vol. 2, 249 (1990). Attempts have been made recently to isolate the S(+)-isomer from the racemic mixture.

U.S. Pat. No. 5,015,764 (assignee: Ethyl Corp.) discloses a process whereby the triethylamine salt of racemic ibuprofen is treated with chiral α-methylbenzylamine (MBA). The MBA salt of one isomer of ibuprofen separates as crystals and is filtered off. The triethylamine salt of the other isomer is isolated from the filtrates, and is separately racemized, which is then treated again as described above.

U.S. Pat. No. 4,994,604 (assignee: Merck & Co.) teaches S-lysine for the resolution of racemic ibuprofen. Racemic ibuprofen and S-lysine are combined in equimolar quantities in a solvent system, such as ethanol:water, so that the solution is supersaturated in both R, S and S, S salts. The solution is first aged at around 30° C., and then seeded at around 25° C. with a fairly large amount of S-ibuprofen-S-lysinate. This allows the S-ibuprofen-S-lysinate from the racemate mixture to crystallize out. The mother liquor, after filtration, is seeded again to precipitate additional S-salt. Repetition of this process gives the S-ibuprofen-S-lysinate as crystals, and leaves the R-salt in the solution, thus allowing a recovery of 50% of the original amount of the racemic ibuprofen as S-ibuprofen lysinate salt.

Other methods such as enzymatic resolution and chromatography have also been suggested for resolution. The disadvantage with such processes is that they are time-consuming, and the yields are low.

While resolution of racemic mixtures is known, generally such processes lead to yields of a maximum 50% of one isomer, and 50% of the other isomer. In order to get higher yields of one isomer, the other isomer, after isolation, must be separately racemized to eventually isolate more of the desired isomer. Such processes generally employ conditions that are so different from the resolution step that the two are incompatible for efficient recycle. Because optically active α-aryl carboxylic acids and their salts have greater commercial value than racemic acids and their salts, there is a growing interest in finding improved methods to selectively crystallize such salts from solutions containing the racemic acid and a chiral amine.

SUMMARY OF INVENTION

The inventive process includes selectively crystallizing a salt of optically active α-aryl carboxylic acid in more than 50% yields with recycle and in high enantiomeric excess from a solution typically containing the racemic form of the same acid and a suitable optically active amino acid. Suitable amino acids include optically active lysine, arginine, histidine. The α-aryl carboxylic acid is of the formula Ar(R)CHCO$_2$H, wherein R is selected from the group consisting of C$_1$-C$_8$ alkyl and C$_1$-C$_8$ substituted alkyl, and Ar is selected from the group consisting of phenyl, substituted phenyl, 2-naphthyl, substituted 2-naphthyl, 2-fluorenyl, and substituted 2-fluorenyl. The inventive process includes (a) forming a solution of a mixture of enantiomers of α-aryl carboxylic acid in a suitable solvent; (b) adding a suitable optically active amino acid such that the amount of said amino acid is not more than about a molar equivalent of the desired enantiomer in said racemic acid; (c) optionally seeding the above mixture with pure crystals of the salt of said α-aryl carboxylic acid and said amino acid and letting it to form crystals of the desired salt typically at a temperature range of about −10° C. to 10 ° C. over a period of about 0.25–8 hours; (d) separating the crystals of the desired salt enriched in one enantiomer of said acid; (e) substantially evaporating the solvent to isolate the other enantiomer of the α-aryl carboxylic acid; (f) racemizing said other enantiomer of step (e) to give racemic α-aryl carboxylic acid which is then recycled to step (a) of the next batch, thus ultimately converting all racemic α-aryl carboxylic acid into almost exclusively the salt of one enantiomer; and (g) optionally acidifying the salt of step (f) to liberate free optically active α-aryl carboxylic acid.

The inventive process is described in detail below in connection with selective crystallization of the L-lysinate salt of S(+)-ibuprofen from typically racemic ibuprofen and L-lysine. [The term S-ibuprofen and S(+)-ibuprofen are hereinafter used interchangeably, as are the terms R-ibuprofen and R(−)-ibuprofen.] Although the instant invention is described herein as a process for resolving racemic ibuprofen, it is potentially useful to prepare optically active α-aryl carboxylic acids in general whether or not the initial acid feed is racemic.

BRIEF DESCRIPTION OF DRAWINGS

The invention is described in detail below with reference to the various figures which are flow diagrams of procedures of the present invention as described in the examples which follow.

DESCRIPTION OF THE PREFERRED EMBODIMENTS

Figure 1:
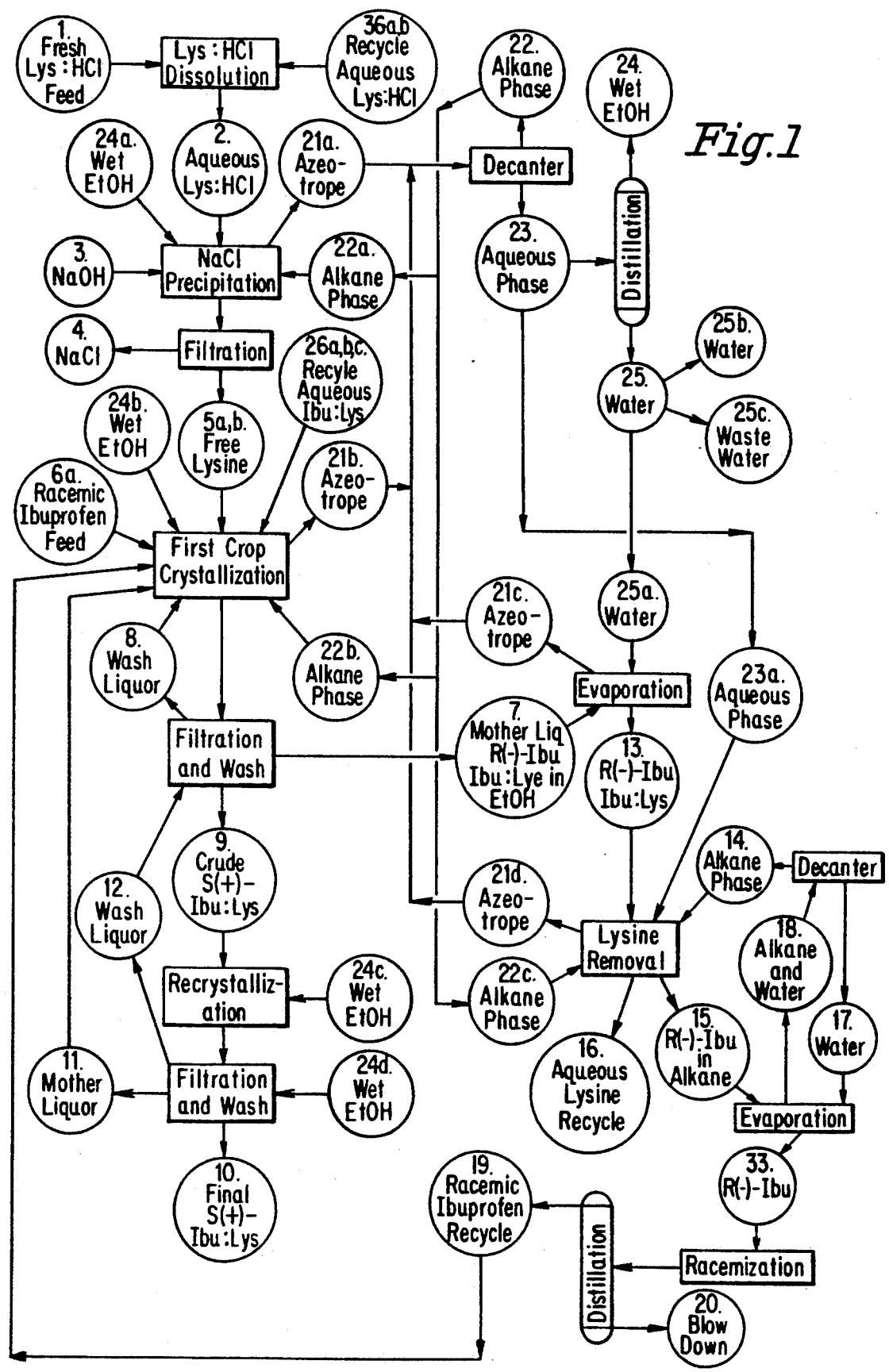

In one embodiment, the invention discloses a novel process to selectively crystallize salts of optically active ibuprofen from solutions containing racemic ibuprofen and an optically active amino acid which forms the salt with the desired enantiomer of ibuprofen. The process, unlike conventional resolution methods, yields, after recycle over several batches, the desired isomer in high yields with high enantiomeric excess, while using not more than about a molar equivalent of the amino acid based on the desired enantiomer of ibuprofen in any single batch. By way of the inventive process, the solution remains unsaturated with respect to the undesired diastereomer. Furthermore, after removing the desired isomer salt from the mix, the undesired isomer of ibuprofen present in the mother liquors is racemized, preferably without any added catalyst or solvent. Such racemization is environmentally desirable, and permits direct recycle of the undesired enantiomer thus ultimately resulting in virtually complete conversion of racemic ibuprofen feed to the salt of the desired enantiomer. The following description illustrates the isolation of the salt of S-ibuprofen.

The process typically begins by forming the salt of racemic ibuprofen with an optically active amino acid such as, for example, L-lysine. The reaction is conducted in a solvent mixture of a suitable alcohol and water. Suitable alcohols are those that can dissolve the ibuprofen and are also miscible with water. Examples include, but are not limited to, methanol, ethanol, n-propanol, isopropanol, 1-butanol, 2-butanol, isobutyl alcohol, t-butyl alcohol, 1-pentanol, 2-pentanol, 3-pentanol, 2-methyl-1-butanol, 2-methyl-2-butanol, 3-methyl-2-butanol, 3-methyl-1-butanol, neopentyl alcohol, and the like, with ethanol and methanol being the preferred, and ethanol the most preferred. Generally the ibuprofen is dissolved in the alcohol to which the requisite amount of an aqueous solution of the amino acid, L-lysine, is added. The amount of water in the total mix ranges generally from 1 parts of water for 99 parts of the alcohol to 10 parts of water for 90 parts of the alcohol, typically from 2 parts of water for 98 parts of the alcohol to 7 parts of water for 93 parts of alcohol, and preferably from 3 parts of water for 97 parts of the alcohol to 5 parts of water for 95 parts of the alcohol. The amount of the amino acid in the mixture is not more than about a molar equivalent of the S(+)-ibuprofen in the racemic acid, typically about 0.6 to 1.0 molar equivalent, and preferably about 0.7-0.9 molar equivalent. The same ratios are preferable with respect to other α-aryl carboxylic acid/amino acid pairs. The concentration of dissolved solids in the alcohol-water mixture ranges from about 3 to about 30 weight %.

The above mixture is then partially distilled with a suitable azeotroping agent to lower the water content of the mixture to about 0.5-7 wt %. Suitable water-immiscible azeotroping agents and organic solvents for this and other steps of the present process include, but are not limited to, benzene, toluene, ethyl benzene, xylene, chlorobenzene, methyl t-butyl ether, ethyl t-butyl ether, ethyl n-butyl ether, di-n-propyl ether, diisopropyl ether, dibutyl ether, methyl acetate, ethyl acetate, propyl acetate, isopropyl acetate, butyl acetate, pentyl acetate, methyl propionate, ethyl propionate, propyl propionate, t-butyl propionate, linear, cyclic or branched pentanes, heptanes, hexanes, octanes, nonanes, and other $C_4$-$C_{10}$ hydrocarbons, ether, and esters, and the like, with cyclohexane, heptane and cycloheptane being the preferred, with cyclohexane and heptane being the most preferred. The mixture is then cooled to about $-10°$ C. to about $10°$ C, preferably at about $-10°$ C. to about $5°$ C., and typically at about $-5°$ C. to about $5°$ C., to start crystallization of S(+)-ibuprofen lysinate salt. The mixture may optionally be seeded with pure crystals of S(+)-ibuprofen lysinate to induce crystallization. Whether seeded or not, the solution is maintained at the above-described temperature for a period of about 0.25-8 hours. If seeding is desired, usually a small amount of seed, a few crystals, is sufficient. The separated first crop crystals of crude S-ibuprofen L-lysinate may be separated by processes such as filtration, centrifugation and the like. This first crop is highly enriched, generally to more than 90%, in the S-form of ibuprofen.

The first crop crystals of crude S(+)-ibuprofen L-lysinate may be recrystallized as follows. The crystals are mixed with an alcohol-water mixture of the types described above, at about 40°-80° C. generally and about 50°-78° C. preferably, to form about a 3-30 wt % mixture. This mixture is then cooled to about $-10°$ C. to about $10°$ C. for about 0.25-8 hours to crystallize pure S(+)-ibuprofen L-lysinate. The mixture may be optionally seeded with the crystals of S(+)-ibuprofen L-lysinate to induce crystallization, if seeding is desired. Enantiomeric purities of more than 99% in the S(+) form of ibuprofen may be obtained.

The filtrates from the first crop filtration contain R-enriched ibuprofen, with small amounts of lysine as the lysinate salt of ibuprofen, and may be processed as follows. The filtrates may be concentrated azeotropically to reduce the water content of the filtrates to about 0.01-3 wt %. This may then be cooled to about 0°-35° C. to deposit a second crop of ibuprofen lysinate. Alternately, a nonsolvent such as, for example, hexane, may be added to the mixture to precipitate the second crop ibuprofen lysinate. This second crop ibuprofen lysinate salt which has an S/R enantiomeric ratio of about 20:80 may then be recycled to the next batch's first crop crystallization of crude S(+)-ibuprofen L-lysinate.

The mother liquors after removing the second crop ibuprofen lysinate salt may be evaporated to leave behind a residue of substantially lysine-free R-enriched ibuprofen which is racemized as described below, and then recycled to first crop crystallization of crude S(+)-ibuprofen lysinate.

Racemization of the R-enriched ibuprofen may be accomplished by several methods. For example, U.S. Pat. No. 5,015,764 referred to above, describes racemization in the presence of triethylamine in octane for 18 hours, or in concentrated hydrochloric acid for 72 hours, or in refluxing isopropanol in the presence of NaOH for 16 hours. U.S. Pat. No. 4,946,997 describes racemization in refluxing isopropyl acetate in the presence of acetic anhydride and sodium acetate, or by heating ibuprofen acid chloride with sodium ibuprofenate. Ruchardt et al., *Angew. Chem. Int. Ed. Engl.*, Vol. 23, page 162 (1964) discloses racemization by refluxing in acetic anhydride and pyridine. While such methods can be used for racemization in the instant case, they, however, have several disadvantages. They generally consume reagents which produce by-products necessitating elaborate separation and waste disposal procedures. They also are carried out in solvents requiring procedures for separation and recovery. Some of the reagents and solvents are also toxic.

It has been found, as an aspect of the present invention, that compositions which consist essentially of an optically active α-aryl carboxylic acid, free from solvents, catalysts, and the like, can be spontaneously racemized by heating under an inert atmosphere. The inert atmosphere may be provided by nitrogen, argon, and the like. The temperature of heating is generally in the range 100°-300° C., typically about 100°-250° C., and preferably about 200°-250° C. The duration of heating is usually about 1-10 hours generally, 2-8 hours typically, and 3-6 hours preferably. As used herein, the term "consisting essentially of" refers to a pure isomer or a mixture of isomers of the same α-aryl carboxylic acid, i.e. the R and S isomers, but specifically excludes other ingredients such as solvents, catalysts, and the like, that would alter the basic and novel characteristics of the invention. The racemization conditions depend on the thermal properties of the material, such as, for example, thermal decomposition characteristics. Such properties may be ascertained by analytical techniques known to those skilled in the art, such as thermal gravimetric analysis, differential scanning calorimetry, and the like. The goal is to find conditions where thermal decomposition of the material during heating would be minimal. The progress and completion of the racemization may be ascertained by analytical techniques such as, for example, chiral High Pressure Liquid Chromatography (chiral HPLC). Heating R-ibuprofen or R-enriched ibuprofen under the above-described conditions effectively converts half of the optically active acid to its mirror image, thus producing the racemic modification as the product. Similar racemization may be performed on S-ibuprofen or S-enriched ibuprofen also.

Racemic ibuprofen obtained from the racemization reaction above may be subjected to selective crystallization as described above to isolate more S-ibuprofen lysinate. Preferably, the racemic ibuprofen from the racemization reaction is vacuum distilled at about 150°-250° C. The distillation residue, with recycles fully implemented, weighs generally about 2% of the final S-ibuprofen lysinate product weight. The distilled, racemized ibuprofen is recycled to the next batch's selective crystallization to isolate more S-ibuprofen lysinate. By combining the racemization and selective crystallization, the inventive process produces S-ibuprofen L-lysinate in yields substantially more than 50%, generally close to 100%, based on the amount of racemic ibuprofen and lysine feeds.

Although the process has been described above for the L-lysinate salt of S(+)-ibuprofen, substantially the same process can be used for selective crystallization of salts of other similar optically active α-aryl carboxylic acids using other similar optically active amino acids. The α-aryl carboxylic acids include, but are not limited to, naproxen, fenoprofen, indoprofen, ketoprofen, flurbiprofen, pirprofen, suprofen, cicloprofen, minoxiprofen, and the like. The amino acids include arginine and histidine.

The S(+)-ibuprofen L-lysinate may optionally be acidified to yield the free S(+)-ibuprofen. Suitable acids include acetic acid, carbonic acid, formic acid, propionic acid, $C_4$-$C_5$ acids, hydrochloric acid, sulfuric acid, and the like. Suitable solvents include hexane, heptane, cyclohexane, xylene, and the other aforementioned solvents. In a typical process, the salt is treated, in a two-phase mixture of an organic solvent and water, with hydrochloric acid. L-Lysine hydrochloride forms and stays in the aqueous layer, while free acid S(+)-ibuprofen stays in the organic layer. The two layers are separated and S(+)-ibuprofen may be isolated by removing the organic solvent. L-Lysine hydrochloride in the aqueous layer may be converted to L-lysine which may then be recycled in the selective crystallization process. If acetic acid is used in the process, L-lysine acetate forms in the process, which may be isolated from the aqueous layer and processed to free L-lysine by lysine acetate cracking described below in the Examples.

The following Examples are provided for purposes of illustration only and not by way of limitation. The various steps described in the examples are illustrated schematically in FIGS. 1-7.

EXAMPLE 1

Precipitation of NaCl from Aqueous Lysine

Referring to FIG. 1, a mixture containing L-lysine hydrochloride (53.48 g, 0.2928 mole) and water (53.48 g) [stream 2, FIG. 1] is added to a stirred mixture containing sodium hydroxide (11.71 g, 0.2928 mole) [from stream 3] and ethanol (221.3 g) [from stream 24a] at 60° C. Heptane [stream 22a] and ethanol [stream 24a] are added to the resulting stirred mixture as an azeotrope [stream 21a] of water, ethanol, and heptane is removed by distillation at atmospheric pressure until the weight ratio of water:ethanol:lysine is lowered to 7:93:17.988. The resulting mixture is filtered hot to remove a solid [stream 4, 17.11g] consisting mostly of NaCl from a solution [stream 5a] containing free lysine.

EXAMPLE 2

First Crop Crystallization of S(+)-Ibuprofen Lysinate from Racemic Ibuprofen in Aqueous Ethanol To a stirred mixture containing S(+)-ibuprofen (0.538 moles, 110.98 g), R(−)-ibuprofen 0.597 moles, 123.11 g), L-lysine (0.43023 moles, 62.895 g), ethanol (606 g), and water (ca. 125 g) [from streams 5a, b; 6a; 8; 11; 19; 24b; and 26a, b, c; FIG. 1]is added heptane [from stream 22b] and ethanol [from stream 24b] as an azeotrope [stream 21b] of water, ethanol, and heptane is removed by distillation at atmospheric pressure until the weight ratio of water: ethanol: lysine is lowered to 6:94:9.747. The stirred, undistilled residue is cooled to 25° C. and seeded with S(+)-ibuprofen lysinate crystals (143 mg). The stirred mixture is seeded with two additional 143 mg portions of S(+)-ibuprofen lysinate crystals, one after the stirred mixture has been cooled further to 0° C. and the other fifteen minutes later. After the mixture is stirred at 0° C. for 4 hours, the resulting precipitate is filtered from the mother liquor [stream 7] and then washed with a mixture [stream 12] containing ethanol (138 g) and water (12 g). The washed precipitate [stream 9] is the first crop crude S(+)-ibuprofen lysinate (0.3442 mole, 121.32 g dry basis) with an ibuprofen S/R ratio of 94:6. The wash liquor [stream 8] is recycled to the next batch's first crop crystallization of S(+)-ibuprofen lysinate.

EXAMPLE 3

Recrystallization of S(+)-Ibuprofen Lysinate

First crop crude S(+)-ibuprofen lysinate [stream 9, FIG. 1, 0.3442 mole, 121.32 g dry basis] is dissolved in a stirred mixture [stream 24c, FIG. 1] containing ethanol (357 g) and water 31 g) at 70°. The resulting stirred mixture is cooled to 25° C., seeded with S(+)-ibuprofen lysinate monohydrate crystals (200 mg), and then cooled further to 0° C. for 4 hours. The resulting precipitate is filtered from the mother liquor [stream 11] and then washed with a mixture [stream 24d] containing ethanol (138 g) and water (12 g). The washed precipitate [stream 10] is pure S(+)-ibuprofen lysinate monohydrate (0.2837 mole, 100 g dry basis) with an ibuprofen S/R ratio of ν99.5:1. The wash liquor [stream 12] is used to wash the next batch's crude S(+)-ibuprofen lysinate from first crop crystallization.

EXAMPLE 4

Evaporation of Solvent from the Mother Liquor of First Crop Crystallization

Water and ethanol are removed as azeotrope stream 21c by distillation in a evaporator from a mixture [stream 7; FIG. 1] containing S(+)-ibuprofen (0.2145 moles, 44.25 g), R(−)-ibuprofen (0.5763 moles, 118.89 g), L-lysine (0.08603 moles, 12.577 g), ethanol (ca. 570 g), and water (ca. 36.4 g). During the distillation, water [30 g, stream 25a] is injected into the base of the evaporator to help strip out the last traces of ethanol and to prevent formation of amides and ethyl esters. The molten evaporation residue [stream 13] contains S(+)-ibuprofen (0.2145 moles, 44.25 g), R(−)-ibuprofen (0.5763 moles, 118.89 g), and L-lysine (0.08603 moles, 12.577 g).

EXAMPLE 5

Second Crop Crystallization of Ibuprofen Lysinate

Figure 2:
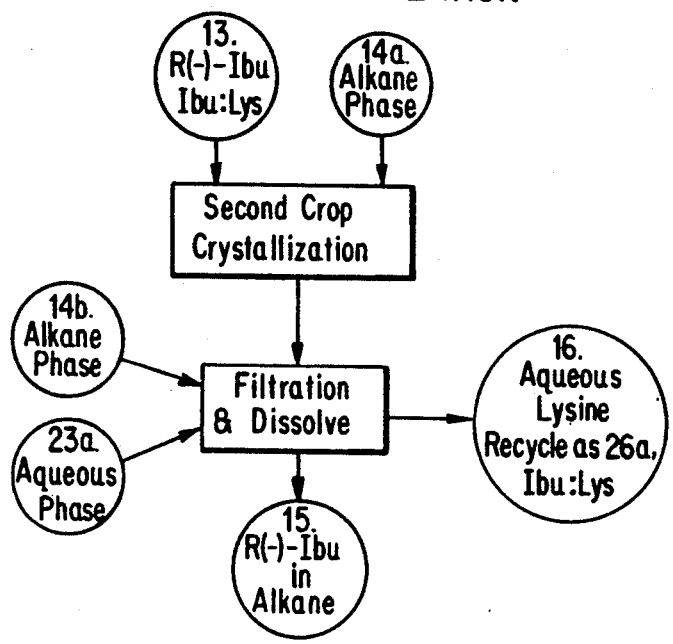
Figure 3:
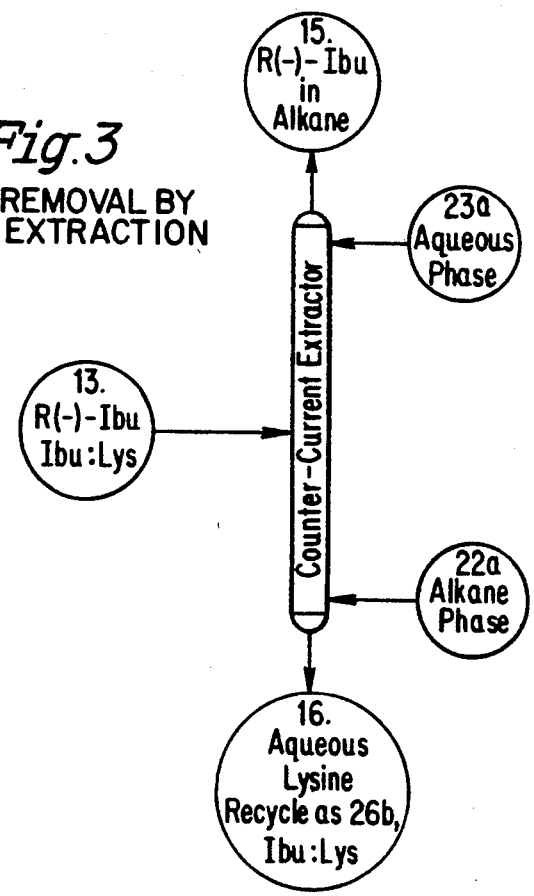
Figure 4:
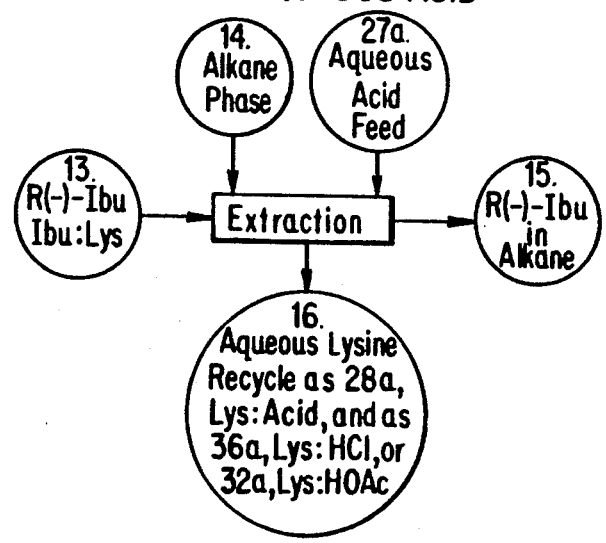

A molten mixture [stream 13, FIG. 2] containing S(+)-ibuprofen (0.2145 moles, 44.25 g), R(−)-ibuprofen (0.5763 moles, 118.89 g), and L-lysinate (0.08603 moles, 12.577 g) is added to heptane [350 g. stream 14a] heated to 50° C. The resulting mixture is stirred for fifteen minutes and then filtered at 50° C to remove precipitated ibuprofen lysinate from the mother liquor. The filtered solid is washed with heptane [50 g, stream 14b]. The mother and wash liquors are combined to provide a mixture [stream 15] containing S(+)-ibuprofen (0.1912 moles, 39.43 g) and R(−)-ibuprofen (0.5136 moles, 105.95 g). The washed filtered solid is a second crop of ibuprofen lysinate and is dissolved in a mixture [stream 23a] containing water (15 g), ethanol (76 g), and heptane (9 g). The resulting aqueous mixture [stream 16] contains ibuprofen lysinate (0.08603 moles, 30.32 g, ibuprofen S/R ratio of 27:73) and is recycled as stream 26a to the next batch's first crop crystallization of crude S(+)-ibuprofen lysinate.

EXAMPLE 6

Racemization and Distillation of R(-)-Enriched Ibuprofen

Heptane is removed as stream 18, FIG. 1, by distillation in an evaporator at atmospheric pressure from a mixture [stream 15, FIG. 1] containing S(+)-ibuprofen (0.1912 moles, 39.43 g), R(−)-ibuprofen (0.5136 moles, 105.95 g), and heptane (ca. 390 g). During the distillation, water [30 g, stream 17] is injected into the base of the evaporator to help strip out the last traces of heptane and to minimize formation of ibuprofen ethyl ester. The molten evaporation residue [stream 33], which contains ibuprofen with an S/R ratio of 27/73, is first racemized by being heated under nitrogen at 220° C. for four hours and is then distilled at about 220° C., 10 mm HgA in an evaporator to provide a distillate [stream 19] of substantially pure racemized ibuprofen (0.6907 moles, 142.48 g. S/R ratio of 47:53) and an undistilled residue [stream 20, 2.91 g] for incineration as a waste stream. Racemized ibuprofen distillate [stream 19] is recycled to the first crop crystallization of crude S(+)-ibuprofen lysinate.

Heptane/water distillate stream 18 is allowed to phase in decanter to provide a heptane upper phase [stream 14] and a water lower phase [stream 17].

EXAMPLE 7

Separation of Azeotrope Streams

Azeotrope distillate streams 21a-d are combined and allowed to separate into two liquid phases inside a decanter (FIG. 1). The alkane upper phase [stream 22] is a 94.8:5.0:0.2 mixture by weight of heptane, ethanol, and water. The aqueous lower phase [stream 23] is a 75.9:15.0:9.1 mixture by weight of ethanol, water, and heptane, a portion of which provides stream 23a. The remainder of the aqueous lower phase [stream 23] is distilled to provide a 92:8 by weight overhead mixture [stream 24] of ethanol and water and a heavy end [stream 25] of substantially pure water. A portion of heavy end water stream 25 is waste water stream 25c, which could be used as a pure water feed for other processes.

EXAMPLE 8

Extraction of Ibuprofen Lysinate from the Crystallization Liquor's Evaporation Residue with Water This procedure is an alternative to the above-described second crop crystallization of crude ibuprofen lysinate (Example 5). A molten mixture [stream 13, FIGS. 1, 3] containing S(+)-ibuprofen (0.2145 moles, 44.25 g), R(−)-ibuprofen (0.5763 moles, 118.89 g) and L-lysine (0.08603 moles, 12.577 g) is injected into the middle of a York-Scheibel-type counter-current extractor fed at the top with a mixture [stream 23a] containing water (15 g), ethanol (76 g), and heptane (9 g) and at the bottom with a mixture [stream 22c] containing heptane (350 g), ethanol (18.5 g), and water (0.73 g). The aqueous lower phase removed from the bottom of the extractor is a mixture [stream 16] containing ibuprofen lysinate (0.08603 moles, 30.32 g, ibuprofen S/R ratio of 27:73) and is recycled as stream 26b to the next batch's first crop crystallization of crude S(+)-ibuprofen lysinate. The alkane upper phase removed from the top of the extractor is a mixture [stream 15] containing S(+)-ibuprofen (0.1912 moles, 39.43 g) and R(−)-ibuprofen (0.5136 moles, 105.95 g) and is evaporated and racemized as described in Example 6, except that the evaporated solvent is recycled as azeotrope stream 21d and not as stream 18.

EXAMPLE 9

Extraction of Ibuprofen Lysinate from the Crystallization Liquor's Evaporation Residue with Aqueous HCl This procedure is an alternative to the above-described second crop crystallization of crude ibuprofen lysinate (Example 5). A molten mixture [stream 13, FIGS. 1, 4] containing S(+)-ibuprofen (0.2145 moles, 44.25 g), R(−)-ibuprofen (0.5763 moles, 118.89 g) and L-lysine (0.08603 moles, 12.577 g) is added to a 50° C. mixture containing heptane (400 g), water (16 g), and HCl (0.08603 mole, 3.137 g) [from streams 14 and 27a]. The resulting mixture is mixed thoroughly and then allowed to phase. The upper phase is a mixture [stream 15] containing ibuprofen (0.7908 moles, 163.13 g; S/R ratio of 27:73) and heptane (ca. 400 g). The lower phase is an aqueous mixture [stream 28a] containing lysine hydrochloride (0.08603 moles, 15.71 g) and is recycled as stream 36a to precipitation of NaCl from aqueous lysine (Example 1).

EXAMPLE 10

Extraction of Ibuprofen Lysinate from the Crystallization Liquor's Evaporation Residue With Aqueous Acetic Acid This procedure is an alternative to the above-described second crop crystallization of crude ibuprofen lysinate (Example 5). A molten mixture [stream 13, FIG. 4] containing S(+)-ibuprofen (0.2145 moles, 44.25 g), R(−)-ibuprofen (0.5763 moles, 118.89 g) and L-lysine (0.08603 moles, 12.577 g) is added to a 50° C. mixture containing heptane (400 g), water (167 g), and acetic acid (0.08603 mole, 5.166 g) [from streams 14 and 27a]. The resulting mixture is mixed thoroughly and then allowed to phase. The upper phase is a mixture [stream 15] containing ibuprofen (0.7908 moles, 163.13 g; S/R ratio of 27:73) and heptane (ca. 400 g). The lower phase is an aqueous mixture [stream 28a] containing lysine acetate (0.08603 moles, 17.743 g) and is recycled as stream 32a to lysine acetate cracking (Example 13 or 14).

EXAMPLE 11

Figure 5:
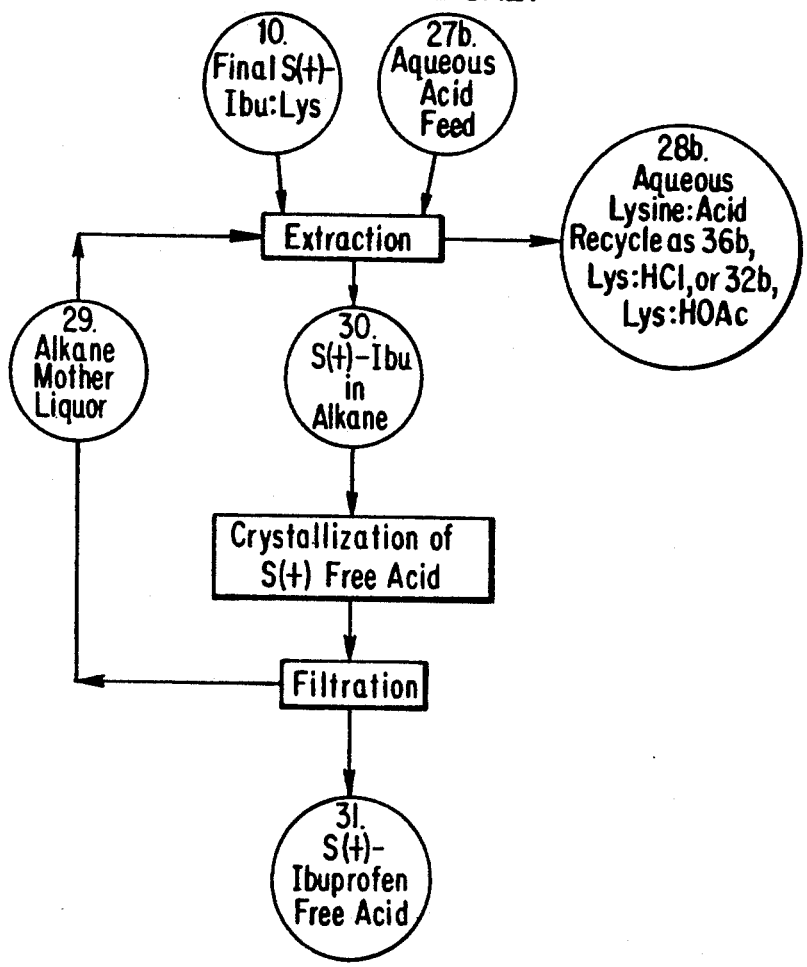

Conversion of S(+)-Ibuprofen Lysinate to S(+)-Ibuprofen Free Acid by Treatment With HCl A mixture of S(+)-ibuprofen lysinate (0.2837 mole, 100 g dry basis), heptane (88 g), S(+)-ibuprofen (8.53 mole, 1.76 g), water (52 g), and HCl (0.2837 mole, 10.344 g) [from streams 10, 27b, and 29, FIG. 5] is mixed thoroughly at 60° C. and then allowed to phase. The lower phase is an aqueous mixture [stream 28b] containing lysine hydrochloride (0.2837 moles, 51.82 g) and is recycled as stream 36b to precipitation of NaCl from aqueous lysine (Example 1). The upper phase [stream 30] is a mixture containing S(+)-ibuprofen free acid (0.2837 moles, 58.524 g) and heptane (ca. 88 g) and is cooled from 60° to 0° C. to crystallize S(+)-ibuprofen free acid. The S(+)-ibuprofen free acid [stream 31, 0.2837 mole, 58.52 g] is removed by filtration from the heptane mother liquor stream 29], which contains S(+)-ibuprofen (8.53 mmole, 1.76 g).

EXAMPLE 12

Conversion of S(+)-Ibuprofen Lysinate to S(+)-Ibuprofen Free Acid by Treatment With Acetic Acid A mixture of S(+)-ibuprofen lysinate (0.2837 mole, 100 g dry basis), heptane (88 g), S(+)-ibuprofen (8.53 mmole, 1.76 g), water (551 g), and acetic acid (0.2837 mole, 17.037 g) [from streams 10, 27b, and 29, FIGS. 1, 5] is mixed thoroughly at 60° C. and then allowed to phase. The lower phase is an aqueous mixture [stream 28b] containing lysine acetate (0.2837 moles, 58.51 g) and is recycled as stream 32b to lysine acetate cracking (Example 13 or 14). The upper phase [stream 30] is a mixture containing S(+)-ibuprofen free acid (0.2837 moles, 58.524 g) and heptane (ca. 88 g) and is cooled from 60° to 0° C. to crystallize S(+)-ibuprofen free acid. The S(+)-ibuprofen free acid [stream 31, 0.2837 mole, 58.52 g] is removed by filtration from the heptane mother liquor stream 29], which contains S(+)-ibuprofen (8.53 mmole, 1.76 g).

EXAMPLE 13

Lysine Acetate Cracking

Figure 6:
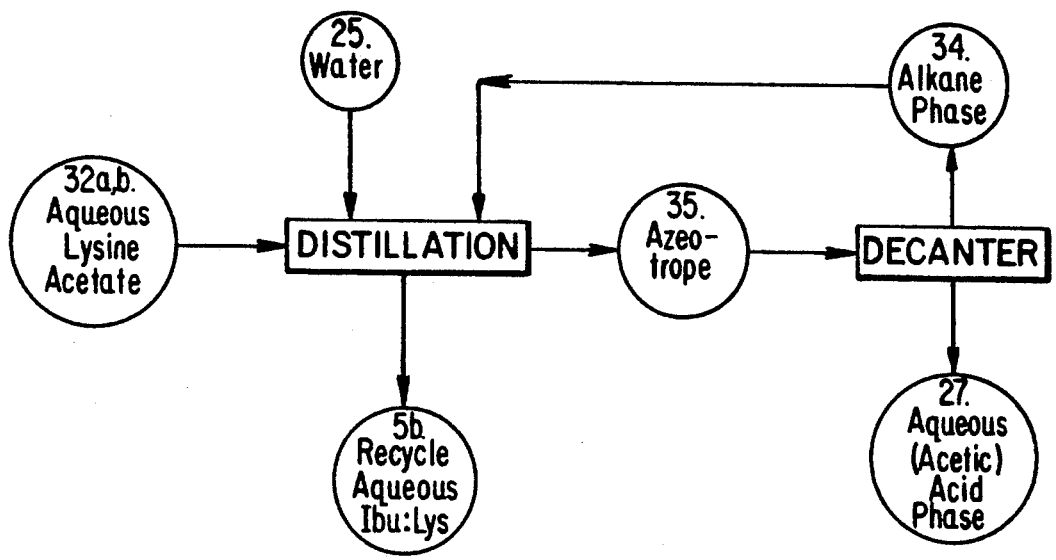

To a stirred mixture [streams 32a,b, FIG. 6] containing lysine acetate (0.36973 moles, 76.254 g) and water (718 g) is added water [stream 25b, 54 g] and heptane [from stream 34] as an azeotrope [stream 35] of water, acetic acid, and heptane is removed by distillation at atmospheric pressure. The distillation residue [stream 5b] contains free lysine (0.36973 moles, 54.05 g) and water (54 g) for recycle to first crop crystallization (Example 2). Distillate stream 35 is allowed to phase in a decanter to provide a heptane upper phase [stream 34] and an aqueous acid lower phase [stream 27] containing acetic acid (0.36973 moles, 22.202 g) and water (718 g).

EXAMPLE 14

Lysine Acetate Cracking with Ibuprofen

Figure 7:
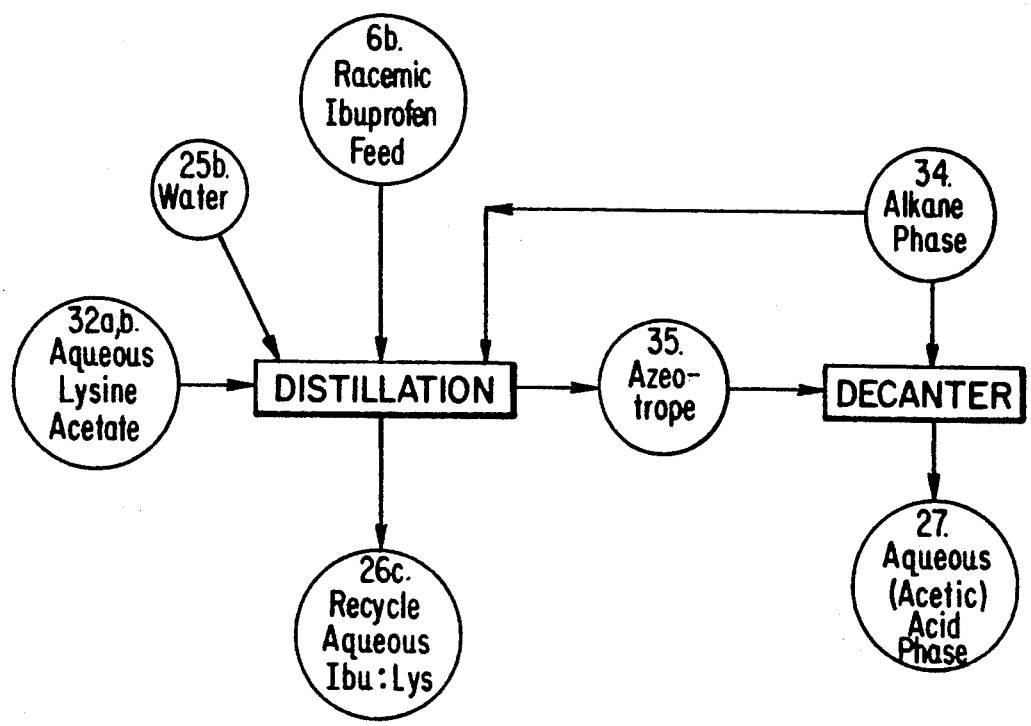

To a stirred mixture containing racemic ibuprofen (0.36973 moles, 76.27 g), lysine acetate (0.36973 moles, 76.254 g) and water (718 g) [from streams 6b and 32a, b, FIG. 7] is added water [stream 25b, 150 g]and heptane [from stream 34] as an azeotrope [stream 35] of water, acetic acid, and heptane is removed by distillation at atmospheric pressure. The distillation residue [stream 26c] contains ibuprofen lysinate (0.36973 moles, 130.32 g) and water (150 g) for recycle to first crop crystallization (Example 2). Distillate stream 35 is allowed to phase in a decanter to provide a heptane upper phase [stream 34] and an aqueous acid lower phase [stream 27] containing acetic acid (0.36973 moles, 22.202 g) and water (718 g).

What is claimed is:

1. A process for racemization of an enantiomerically enriched α-arylcarboxylic acid, said process comprising heating said enantiomerically enriched α-arylcarboxylic acid at about 100°–300° C. for about 1–10 hours, in the substantial absence of other components.

2. A process for racemization of an enantiomerically enriched α-arylcarboxylic acid, said process comprising heating said enantiomerically enriched α-arylcarboxylic acid at about 100°–300° C. for about 1–10 hours, in the substantial absence of solvent.

3. A process for separation of an α-acrylcarboxylic acid of the formula $Ar(R)CHCO_2H$ from an amino acid, said process comprising:
   contacting a starting mixture containing said amino acid and said α-arylcarboxylic acid with an organic acid to produce a salt of said amino acid and said organic acid,
   separating said salt from a material containing said α-arylcarboxylic acid in a proportion to said amino acid that is greater than that in said starting mixture,
   wherein said organic acid is selected from the group consisting of carbonic, formic, acetic, propionic and $C_4$–$C_5$ acids; R is selected from the group consisting of $C_1$–$C_8$ alkyl and $C_1$–$C_8$ substituted alkyl; Ar is selected from the group consisting of phenyl, substituted phenyl, 2-naphthyl, substituted 2-naphthyl, 2-fluorenyl, and substituted 2-fluorenyl; and said amino acid is selected from the group consisting of lysine, arginine, and histidine.

* * * * *